United States Patent [19]

Heinrich et al.

[11] Patent Number: 4,850,976
[45] Date of Patent: Jul. 25, 1989

[54] COMBINATION SHEATH AND FOLDABLE SHIELD FOR HYPODERMIC SYRINGE NEEDLE

[75] Inventors: William P. Heinrich, McHenry; Norbert Leopoldi, Chicago, both of Ill.; Richard Brewer, Belmont, Calif.

[73] Assignee: The Cloverline, Inc., Chicago, Ill.

[21] Appl. No.: 179,051

[22] Filed: Apr. 8, 1988

[51] Int. Cl.$^4$ ............................................. A61M 5/32
[52] U.S. Cl. .................................... 604/192; 604/263
[58] Field of Search ....................... 604/192, 187, 263

[56] References Cited

U.S. PATENT DOCUMENTS 4,573,975  3/1986  Frist et al. .................. 604/192
4,735,617  4/1988  Nelson et al. .
4,735,618  4/1988  Hagen .
4,740,204  4/1988  Masters et al. .
4,767,412  8/1988  Hymanson .

Primary Examiner—John D. Yasko
Attorney, Agent, or Firm—Lloyd L. Zickert

[57] ABSTRACT

A combination sheath and shield for enclosing the needle of a hypodermic syringe and for preventing finger punctures during replacement of the sheath over the syringe needle, which includes a sheath that telescopically encloses the needle and frictionally engages the support portion for the needle and a sheath having foldable flaps that are foldable along the sheath during nonuse for compactness during shipping and storage.

17 Claims, 3 Drawing Sheets

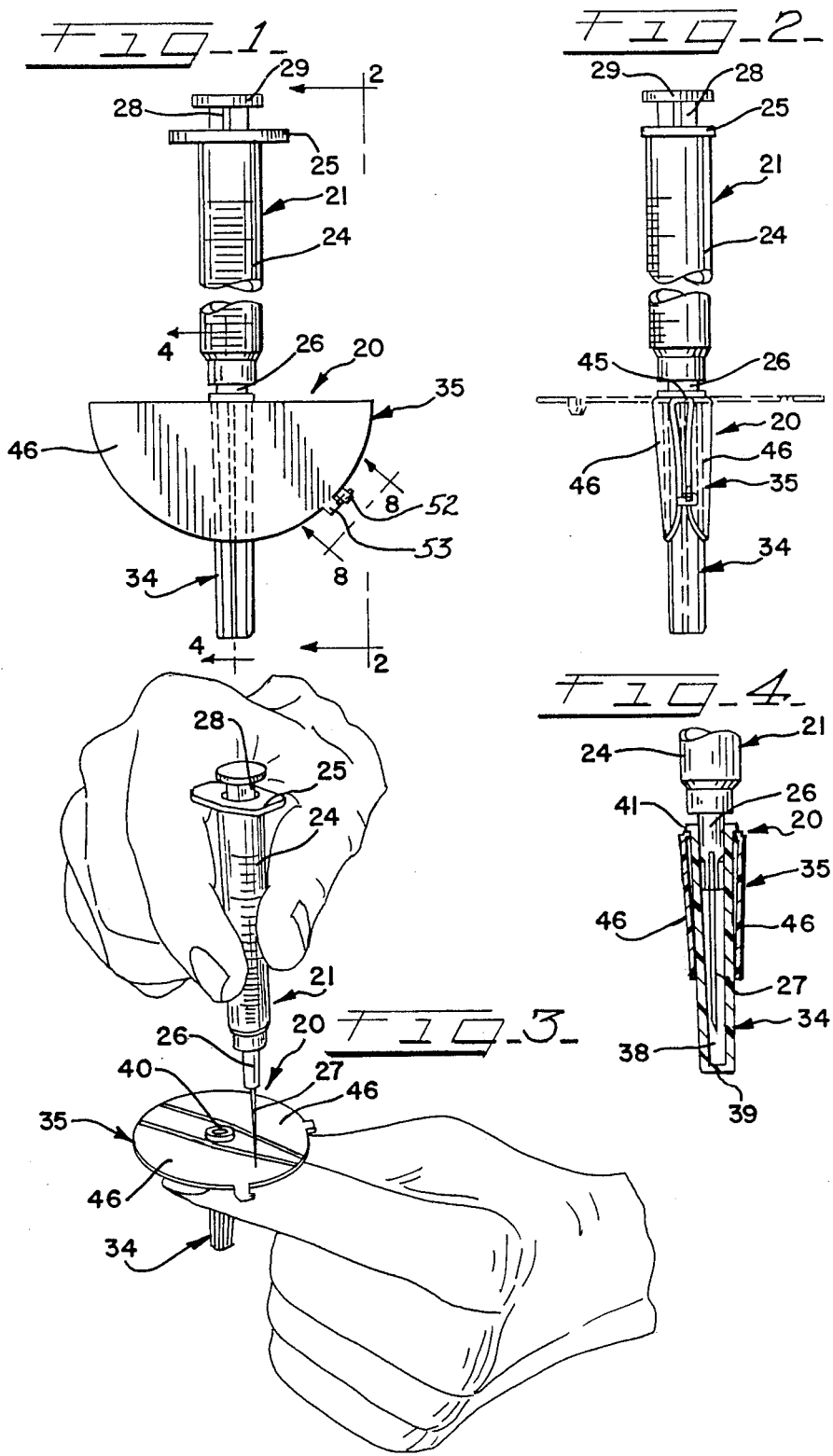

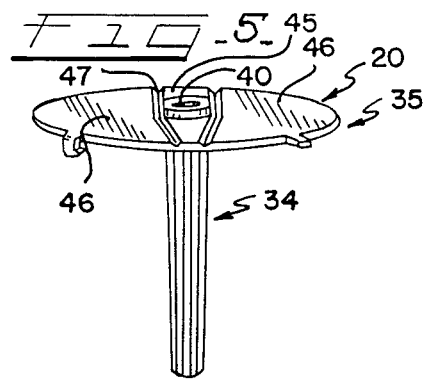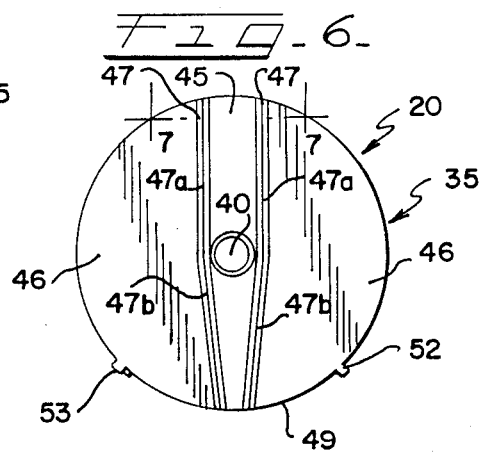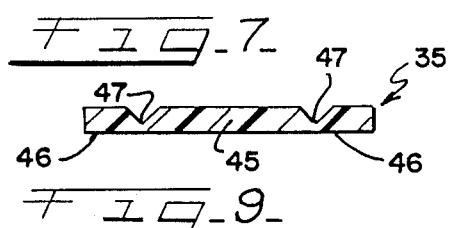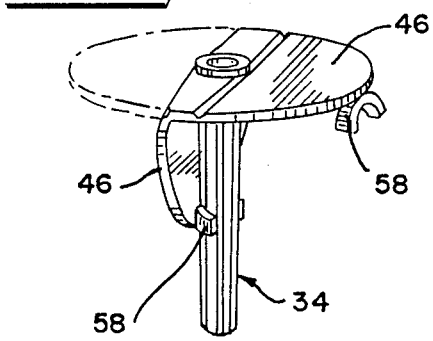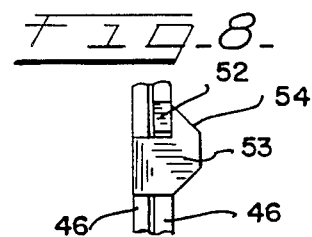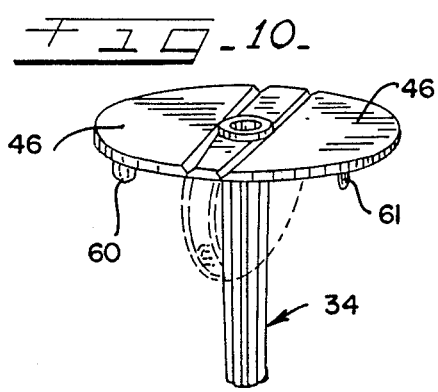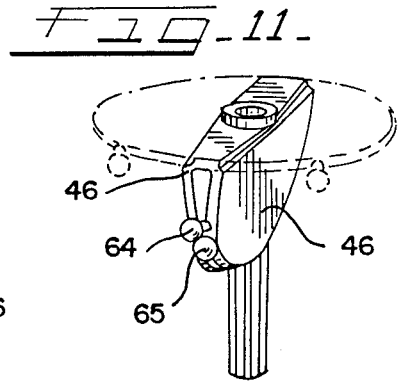

4,850,976

COMBINATION SHEATH AND FOLDABLE SHIELD FOR HYPODERMIC SYRINGE NEEDLE

Description

This invention relates in general to a combination sheath and shield for hypodermic syringe needles, and more particularly to a sheath and shield where the shield is foldable for compactness and storability during nonuse, and still more particularly to a combination sheath and shield where the shield has foldable flaps to enhance shipping and storability.

BACKGROUND OF THE INVENTION

Hypodermic syringes are conventionally provided with a sheath for enclosing the needle to protect it against contamination and breakage during handling. Hypodermic syringes are used heavily by health workers and others for purposes of injecting medication into a person. This process requires filling of the syringe with the medication and thereafter emptying all or part of the contents during an injection procedure. During filling and emptying of the syringe, it is necessary to remove the sheath and replace it. It is during replacing of the sheath, which quite often takes place under hurried and stressful situations, that the health worker will puncture his or her fingers. This is not a serious problem when the needle has not been used, as it is then sterile, but it can be a deadly problem when the needle has been used on a person having a communicable or transmittable disease, as that disease then can be transmitted to the worker using the syringe. For example, it has been known for some workers to have contracted AIDS from such a needle puncture.

Heretofore, there have been a number of proposed sheath constructions directed at solving this problem. For example, funnel-shaped guides have been provided at the inlet end of a sheath. Some sheaths have been constructed so that they can be mounted on a syringe laterally, but they then require secondary sheaths to completely enclose the needle. There also have been some sheaths with relatively small shields attached or formed integrally with the sheath and which function to provide minimal protection against needle punctures. The problem encountered with attempting to provide large shields to better protect against puncture lies in the difficulties encountered in shipping and storing the syringes because they require a great deal of space.

Because of the increasing problems confronting health workers who treat patients with highly communicable diseases and the chance of enduring a needle puncture, it is imperative that a solution be found to protect the health workers.

SUMMARY OF THE INVENTION

The combination sheath and shield of the present invention overcomes the problems heretofore encountered in that the shield is sufficiently large to properly protect the health worker against needle punctures, and it is also collapsible for greatly reducing its size to enhance shipping and storability. While the sheath and shield are integrally formed of a suitable plastic material, it is constructed with the shield being foldable along the sheath so that, when mounted on a hypodermic syringe, the syringe with the sheath and shield can be laid substantially flat. The shield is constructed to have foldable flaps that not only fold along the sheath when in nonuse, but also may be locked in folded position by a suitable latching means. In one form the latching means includes latch members at the edges of the flaps which coact with one another when the flaps are in folded position, and in another form latch members that coact with the sheath to maintain the flaps in folded position. In still another form of latching means, latch members may be provided on the underside of the flaps for coacting with each other while the flaps are in folded position. While it is preferred that the flaps fold downwardly along the sheath, the shield may be disposed lower on the sheaths to allow the flaps to be folded upwardly along the sheath. When the shield is in folded and in latched position and on the syringe, the syringe may be laid flat to facilitate shipping or storage.

It is therefore an object of the present invention to provide a new and improved sheath and shield for enclosing the needle for a hypodermic syringe and for protecting a health worker during replacement of the cap on the syringe against needle punctures.

Another object of the present invention is to provide a combination sheath and shield for enclosing the needle of a hypodermic syringe during nonuse, which includes a sheath for telescopically receiving the needle and a large shield for protecting the fingers of the user against punctures, and which shield is foldable along the sheath during nonuse to enhance compactness for shipping and storing.

A further object of the invention resides in the provision of a combination sheath and shield for enclosing the needle of a hypodermic syringe wherein the shield is integrally formed with the sheath and includes foldable flaps that are foldable along live hinges to lie against the sheath during nonuse and which includes a latching means for latching the flaps in folded position.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is an elevational view of a hypodermic syringe having a sheath and shield according to the present invention mounted on the syringe and enclosing the needle;

FIG. 2 is an elevational view taken substantially along line 2—2 of FIG. 1 to show the folded and latched flaps in solid view and in unfolded position in phantom;

FIG. 3 is a perspective view of the hands of a person during manipulation of the sheath and shield and the hypodermic syringe when replacing the sheath on the needle to illustrate the protection afforded against puncture if the needle is attempted to be wrongly inserted back into the sheath;

FIG. 4 is a vertical sectional view taken through the sheath and shield substantially along line 4—4 of FIG. 1 to also show coaction between the sheath and the needle supporting means when the sheath and shield is in position on the syringe;

FIG. 5 is a perspective view of the sheath and shield removed from the syringe and showing the shield in unfolded and usable position;

FIG. 6 is a top plan view of the sheath and shield of FIG. 5;

FIG. 7 is an enlarged cross-sectional view taken through the shield substantially along line 7—7 of FIG. 6;

FIG. 8 is an enlarged end view of the latching means taken substantially along line 8—8 of FIG. 1;

FIG. 9 is perspective view of a combination sheath and shield having a modified latching means which coacts with the sheath and illustrating one flap in folded position in solid and in open position in phantom;

FIG. 10 is a perspective view of a combination sheath and shield according to the invention having a still further modified latching means which includes a socket on the underside of one of the flaps and a pin on the underside of the other flap which coact when the flaps are in folded position to latch the flaps together;

FIG. 11 is a perspective view of a still further modified latching means in the form of ball locks mounted on the edges of the flaps and illustrating the flaps in solid in folded and latched position and in phantom in open position;

DESCRIPTION OF THE INVENTION

Figure 12:
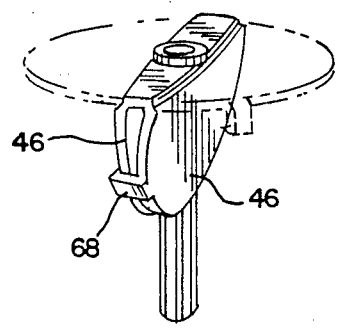
FIG. 12 is a perspective view of the sheath and shield of the present invention and which includes a still further modified latching means in the form of a hook mounted on one of the flaps which engages over the other flap when they are in folded position.

Referring now to the drawings and particularly to FIGS. 1 to 8, one form of the combination sheath and shield according to the invention is illustrated and generally designated by the numeral 20. The combination sheath and shield is illustrated in needle-enclosing position on a hypodermic syringe 21 in FIGS. 1, 2 and 4 and in removed position in FIG. 3. Additionally, the shield is shown in folded position in FIGS. 1, 2 and 4 and in open position in FIG. 3.

It will be understood that the combination sheath and shield of the present invention may be adapted for use on various types of hypodermic syringes to enclose their needles and that only one such type of hypodermic syringe is illustrated, which includes generally a barrel 24 having a finger-engaging flange 25 at the upper end, a needle-supporting means at the lower end in the form of a hub 26, and a needle 27 carried by the hub. A plunger 28 having an end flange 29 is slidably received in the barrel 24. It will be understood that the hypodermic syringes operate in the usual manner in which the plunger is retracted to fill the barrel and later depressed for emptying the contents during an injection procedure. When the syringe is filled, it is necessary to remove the combination sheath and shield so that the needle can be inserted into a medicine bottle in the usual manner. Thereafter, and normally before usage of the syringe for an injection procedure, the combination sheath and shield is replaced on the syringe for protecting the integrity of the needle. During an injection procedure, the sheath and shield is again removed, and after the injection procedure has been completed, the sheath and shield are replaced on the syringe so that it can be disposed of and also to protect against someone accidentally contacting the needle and becoming contaminated with any disease picked up by the needle during use on a diseased person. It is during the time of replacing the sheath and shield following an injection procedure that it is critical to protect the fingers of the user against needle punctures. The sheath and shield of the present invention provides that protection, together with the ability to have the shield collapsible for compactness during shipping and storage, as well as disposal procedures.

The combination sheath and shield 20 includes generally a sheath 34 and a shield 35. It will be appreciated that the sheath and shield may be made separately and thereafter assembled, or they may be made together as an integral structure. Further, they will be made of a suitable plastic material having a suitable flexibility. For example, they may be made of a polypropylene or a linear polyethylene, or any other suitable thermoplastic material. With respect to a hypodermic syringe, its parts are normally made of plastic, except for the needle which is made of metal.

The external surface of the sheath 34 is fluted, although it could be made smooth. Further, it is tapered from the top open end to the bottom closed end, although again it need not be tapered. As seen particularly in FIG. 4, the sheath provides a needle cavity 38 having an end wall 39 at the lower end and an open end or mouth 40 at the upper end, whereby the needle is telescopically received within the cavity. Additionally, at the upper open end of the sheath, or mouth end, it will be formed to frictionally coact with the hub 26 to frictionally retain the shield on the syringe when desired. It will be understood that application of a separating pressure will dislodge the sheath from the hub of the hypodermic syringe when it is desired to use the needle for filling or injecting. A flange 41 is provided at the upper open end of the sheath, although this is not necessary, and when the shield would be integrally made with the sheath, it would not need to be provided.

Figure 17:
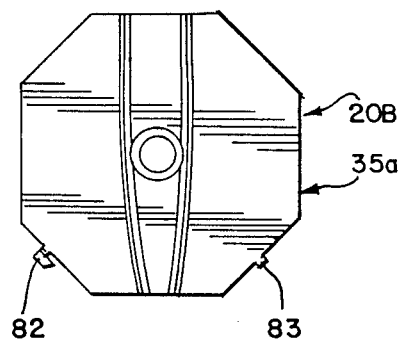
FIG. 17 is a top plan view of a further modified sheath and shield according to the invention wherein the shield is polygonally shaped as opposed to being disk-shaped in the previous embodiments.

The shield 35 includes a stationary portion 45 and two opposite foldable portions or flaps 46. The shield is disk-shaped and essentially circular in form, although it may take other forms and even be polygonal, as shown in FIG. 17. The flaps are interconnected with the stationary portion 45 by means of living hinges 47. Each living hinge includes portions 47a that are parallel to each other and portions 47b that are non-parallel and which converge toward the outer edge 49 of the shield. The converging sections 47b, as will be more clearly hereinafter explained, allow the adjacent portions of the flaps to come closer together in order to permit latching means to more easily operate. Thus, the segments 47a extend approximately half way across the shield, and segments 47b extend approximately half way across the shield. However, the living hinges may be parallel across the entire shield, as seen by the embodiment in FIG. 15.

It is also important that the size of the shield be such as to adequately protect the fingers during replacement of the sheath on the syringe. The shield of the present invention is about eight times greater in dimension than the outer dimension of the sheath. It must be at least four times greater, but preferably about eight times.

Latching means is mounted on the outer edge of the shield and, in this embodiment, includes a tab 52 mounted on one of the flaps, and a hook 53 mounted on the other flap, which coact to selectively latch the flaps together when they are folded alongside of the sheath. The hook and tab are shown in latched position in FIGS. 1, 2, and 8. As seen particularly in FIG. 8, the hook is provided with a cam surface 54 over which the tab cams or slides when it moves into hooked position, as shown in FIG. 8. The flexibility of the flaps by virtue of the material from which they are made allows the tab to move up the cam or ramp 54 when the flaps are moved toward each other and then over into hooked position, thereby retaining the flaps in folded position. Thus, merely pushing the flaps toward each other into folded position will effect the latching, and when it is desired to open the flaps, it is only necessary to apply finger pressure between the flaps in order to cause an unlatching and then separating of the flaps so that they move to open position. Positioning of the fingers under the shield and around the sheath automatically holds the flaps in open position and in a shielding position to shield the fingers against needle puncture. However, the flaps will spring toward open position when unlatched.

As seen particularly in FIG. 7, the living hinges 47 are preferably formed by a groove being provided along the top surface of the shield to facilitate the downward folding of the flaps. A living hinge is well known for plastic materials, and it relates to an area along the material that permits ease of bending of the material. It should be appreciated that the shield may be made of separate parts with other types of hinge means and still be within the scope of the present invention.

It will now be best understood that the operation of the sheath and shield of the present invention is such that when it is initially made by a manufacturer and prepared for shipping, the flaps will be moved to folded position. It is then received by the user, who opens the flaps when it is desired to put the shield into operation to protect the fingers of the user. Thereafter, again when it is desired for storing the hypodermic syringe with the shield and sheath thereon, the shield is folded so that the overall device is more compact, and whereby it will be appreciated that the hypodermic syringe with the sheath and shield can be laid flat.

A modified latching means for retaining the flaps in folded position is shown in the embodiment of FIG. 9, which includes clips 58 mounted on the underside of the flaps 46 which coact with the sheath to hold the flaps in folded position. Thus, the clips 58 which may be placed in staggered position so that they do not interfere with one another when the flaps are in folded position are formed to snap fit over the sheath 34 when in folded position. It will be understood that they may easily be unsnapped when desiring to open the shield by applying pressure to the backsides of the flaps.

Another form of latching means is illustrated in the embodiment of FIG. 10, wherein the latching means includes a socket 60 mounted on the underside of one of the flaps 46 and a pin 61 mounted on the underside of the other of the flaps 46 which coacts to be frictionally received in the socket 60 when the flaps are in closed position as shown in dotted lines to retain the flaps in closed position. It will be appreciated that the socket and pin are positioned so that they will align at one side of the sheath when the flaps are moved to folded position.

Another form of latching means is illustrated in FIG. 11, wherein ball locks are mounted on the edges of the flaps and which includes ball locks 64 and 65 that extend from the edges of the flaps and which, when the flaps are brought together, overlap in locking position. The flaps 46 in FIG. 11 are shown in folded position in solid lines and in phantom in open position to illustrate the operation of the latching means. It will be appreciated that from the latching position, it is a simple matter to apply pressure to the balls 64 and 65 to disengage them and allow the flaps to open.

Another form of latching means is illustrated in FIG. 12, which includes a hook 68 mounted on the edge of one of the flaps 46 and formed so that when the flaps are brought into folded position, it will snap over the edge of the other flap and retain them in locked position.

Figure 13:
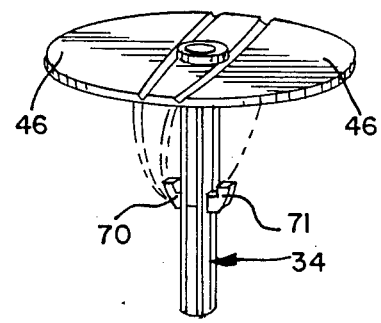
FIG. 13 is a perspective view of a combination sheath and shield according to the present invention which includes a still further modified latching means in the form of hooks mounted on the sheath that latchably engage the edges of the flaps when they are in folded position.

A still further form of latching means is illustrated in FIG. 13, which includes a pair of hooks 70 and 71 mounted on the opposite sides of the sheath 34, and which coact with the edges of the flaps 46 when they are brought into folded position, as seen in phantom.

Figure 14:
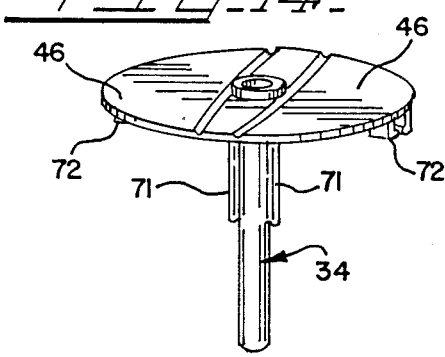
FIG. 14 is a perspective view of a combination sheath and shield according to the invention with a still further modified latching means in the form of ribs on the sheath and clips on the undersides of the flaps which engage the ribs when they are in folded position.

A still further type of latching means is illustrated in FIG. 14. In this embodiment, the sheath 34 is provided with a smooth exterior face, and the latching means includes opposed ribs 71 formed on the sheath to coact with clips 72 formed on the undersides of the flaps 46, so that when the flaps are folded downwardly, the clips engage the ribs and hold the flaps in folded position.

Figure 15:
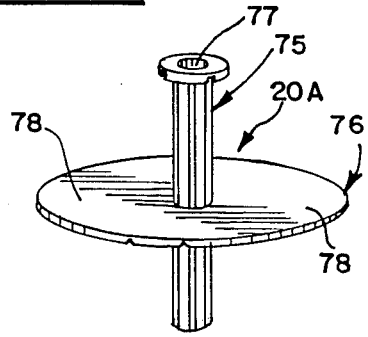
FIG. 15 is a perspective view of a modified combination sheath and shield according to the invention where the shield is spaced below the open end of the sheath and the foldable flaps swing upwardly into stored position.
Figure 16:
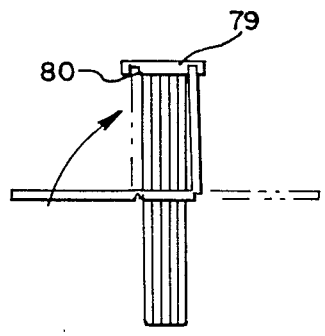
FIG. 16 is an end elevational view of the sheath and shield of FIG. 15 and showing the manner in which the flaps are latchable into folded position by providing a flange at the open end of the sheath with notches for receiving the edges of the flaps when they are in folded position.

A further modified sheath and shield according to the present invention, and generally designed by the numeral 20A, is shown in FIGS. 15 and 16. The sheath is generally designated by the numeral 75, and shield by the numeral 76. The shield is mounted in spaced relation below the upper open end 77 of the sheath. The shield is spaced downwardly from the upper open end so that the flaps may be folded upwardly along the sheath. The flaps are identified as 78 and the latching mechanism includes a flange 79 at the upper end of the sheath having notches 80 for receiving the edges of the flaps when they are in upward folded position, as illustrated particularly in FIG. 16. Other than folding of the flaps upwardly, the sheath and shield combination is used in the same manner as the other embodiments in that the sheath telescopically covers a syringe needle, and the shield protects the fingers against punctures from the needle during replacement of the sheath on the syringe.

Another embodiment of the invention is shown in FIG. 17 and generally designated by the numeral 20B, which differs from the sheath and shield 20 of FIGS. 1 to 8 only in that the shield, designated 35a, is polygonal in shape. When viewed from the top, as illustrated, it is octagonal, although it may have any desired number of sides. A latching means in the same form as that shown in the first embodiment having a hook 82 and a tab 83 is provided for latching the flaps in closed position. This embodiment operates in the same manner as the embodiment of FIGS. 1 to 8.

In view of the foregoing, it is appreciated that the sheath and shield of the present invention provides a high degree of protection to the user against finger punctures and also allows ease of shipping and storage by being compactible into a structure that can allow the entire assembly of the syringe and the sheath and shield to lay flat. Thus, the foldable flaps permit the ease of shipping and storing of the unit as a whole.

It will be understood that modifications and variations may be effected without departing from the scope of the novel concepts of the present invention, but it is understood that this application is to be limited only by the scope of the appended claims.

The invention is hereby claimed as follows:

1. A combination sheath and shield for enclosing the needle of a hypodermic syringe, wherein the syringe includes a needle and needle-supporting means for the needle, said sheath and shield comprising, a sheath having a cavity means for telescopically receiving and enclosing the needle and at least a part of the needle supporting means, a shield disposed along the sheath sized to protect fingers gripping the sheath, said shield including portions foldable and storable along the sheath when not being used to render the sheath and shield compact for shipping and storage, said shield further including a stationary portion on the sheath, and hinge means between the foldable portions and said stationary portion.

2. The combination of claim 1, wherein said shield is made of plastic, and said hinge means is a living hinge.

3. A combination sheath and shield for enclosing the needle of a hypodermic syringe, wherein the syringe includes a needle and needle-supporting means for the needle, said sheath and shield comprising, a sheath having a cavity means for telescopically receiving and enclosing the needle and at least a part of the needle supporting means, a shield disposed along the sheath sized to protect fingers gripping the sheath, said shield including portions foldable and storable along the sheath when not being used to render the sheath and shield compact for shipping and storage, means for selectively holding the foldable portions in stored position along the sheath, said holding means including a latch device having a first latch member on one of said foldable portions and a second latch member on the other of said foldable portions.

4. The combination of claim 3, wherein said latch members coact with each other.

5. The combination of claim 3, wherein said latch members coact with said sheath.

6. The combination of claim 3, wherein said holding means includes tabs on the sheath coacting with the edges of said foldable portions.

7. The combination of claim 1, wherein the stationary portion extends substantially perpendicular to said sheath.

8. The combination of claim 7, wherein said stationary portion is integral with the sheath.

9. The combination of claim 3, wherein one of said latching members includes a socket and the other of said latching members includes a pin for frictionally engaging the socket to hold the foldable portion in folded position.

10. The combination of claim 3, wherein said latch members are ball-shaped and mounted on the edges of the foldable portions.

11. The combination of claim 3, wherein one of the latch members is a tab mounted on the edge of one of the foldable portions, and the other of said latch members is a hook mounted on the edge of the other of the foldable portions.

12. A combination sheath and shield for enclosing the needle of a hypodermic syringe, wherein the syringe includes a needle and needle-supporting means for the needle, said sheath and shield comprising, a sheath having a cavity means for telescopically receiving and enclosing the needle and at least a part of the needle supporting means, and a shield disposed along the sheath sized to protect fingers gripping the sheath, said shield including a stationary portion extending substantially perpendicular to said sheath having a width about equal to the width of the sheath, and a pair of flaps extending from said stationary portion and foldable and storable along the sheath when not being used to render the sheath and shield compact for shipping and storage, said flaps being integral with said stationary portion and connected by living hinges.

13. The combination of claim 12, wherein said shield further includes latch means for retaining the flaps in folded position along the sheath.

14. The combination of claim 13, wherein the latch means includes a first latch member at an edge of one flap and a second latch member at an edge of the other flap.

15. The combination of claim 14, wherein said latch members are outward of one side of said sheath, and said living hinges at said one side are closer together than at the other side.

16. The combination of claim 15, wherein the shield is more than four times larger in transverse dimension than the sheath.

17. The combination of claim 15, wherein the shield is about eight times larger in transverse dimension than the sheath.

* * * * *